United States Patent
Kaercher et al.

(10) Patent No.: US 10,206,756 B2
(45) Date of Patent: Feb. 19, 2019

(54) TOOL FOR A DISMANTLABLE MEDICAL INSTRUMENT

(71) Applicant: KARL STORZ GmbH & Co. KG, Tuttlingen (DE)

(72) Inventors: Daniel Kaercher, Radolfzell (DE); Jochen Stefan, Wald (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 314 days.

(21) Appl. No.: 15/164,942

(22) Filed: May 26, 2016

(65) Prior Publication Data

US 2016/0346057 A1    Dec. 1, 2016

(30) Foreign Application Priority Data

May 26, 2015   (DE) .......................... 10 2015 108 219

(51) Int. Cl.
*A61B 90/00* (2016.01)
*A61B 17/29* (2006.01)
*A61B 17/00* (2006.01)

(52) U.S. Cl.
CPC ........ *A61B 90/08* (2016.02); *A61B 17/00234* (2013.01); *A61B 17/29* (2013.01); *A61B 2017/00296* (2013.01); *A61B 2017/00477* (2013.01); *A61B 2017/294* (2013.01); *A61B 2017/2931* (2013.01)

(58) Field of Classification Search
CPC ............ A61B 17/29; A61B 2017/2902; A61B 2017/2903; A61B 2017/2926; A61B 2017/2931; A61B 2017/2932; A61B 2017/2946; A61B 2017/2939; A61B 17/28; A61B 17/282
USPC .................................................. 606/205, 207
See application file for complete search history.

(56) References Cited

U.S. PATENT DOCUMENTS 8,882,750 B2 * 11/2014 Stefan ................. A61B 17/29
606/1
2013/0304083 A1   11/2013 Kaercher et al.
2013/0310865 A1   11/2013 Merz et al.

FOREIGN PATENT DOCUMENTS

| DE | 10 2013 211 368 A1 | 12/2014 |
| EP | 2 653 110 A1 | 10/2013 |
| EP | 2 653 123 A1 | 10/2013 |
| WO | WO 2010/114634 A1 | 10/2010 |

* cited by examiner

*Primary Examiner* — Eric Rosen
*Assistant Examiner* — Chima Igboko
(74) *Attorney, Agent, or Firm* — Muncy, Geissler, Olds & Lowe, P.C.

(57) ABSTRACT

A tool for a dismantlable medical instrument includes a first component, which surrounds a cavity for receiving a distal end of a shank, and a second component with a catch, which protrudes into the cavity surrounded by the first component to form a bayonet connection with a distal end of a shank protruding into the cavity, by engagement of the catch in a slit or a groove at the distal end of the shank. The first component has a recess into which the second component is fitted.

13 Claims, 3 Drawing Sheets

TOOL FOR A DISMANTLABLE MEDICAL INSTRUMENT

This nonprovisional application claims priority under 35 U.S.C. § 119(a) to German Patent Application No. 10 2015 108 219.5, which was filed in Germany on May 26, 2015, and which is herein incorporated by reference.

BACKGROUND OF THE INVENTION

Field of the Invention

The present invention relates to a tool for a dismantlable medical instrument, and to a dismantlable medical instrument.

Description of the Background Art

Laparoscopic and other micro-invasive medical procedures should be able to be performed through the smallest possible natural or artificial body openings and within the smallest possible cavities. Extremely thin medical instruments are required for this purpose. Moreover, for cleaning and sterilizing the tool after use and before a subsequent use, it is necessary or at least desirable that the instruments are able to be dismantled to the greatest possible extent.

As the process of miniaturization continues, known and established concepts for releasable mechanical connection of several components of a dismantlable medical instrument are scalable only to a limited extent. Therefore, new concepts concerning the dismantlable nature of medical instruments have to be developed.

SUMMARY OF THE INVENTION

It is therefore an object of the present invention to make available an improved tool, in particular one capable of further miniaturization, for a dismantlable medical instrument, and also an improved dismantlable medical instrument, in particular one capable of further miniaturization.

In an exemplary embodiment, on a tool for a dismantlable medical instrument, catches provided for a bayonet connection to the distal end of a shank do not protrude outward but instead inward. The catches are therefore provided to engage not from the inside, but from the outside, in slits or grooves at a distal end of a shank. The technical manufacturing problem arising here is solved in particular by the fact that the catches are not manufactured together with a component that forms a cavity for receiving the distal end of a shank. Rather, only recesses for the catches are initially provided in the component, into which recesses the catches are then inserted and are secured.

An exemplary tool for a dismantlable medical instrument comprises a first component, which surrounds a cavity for receiving a distal end of a shank, and a second component with a catch, which protrudes into the cavity surrounded by the first component to form a bayonet connection with a distal end of a shank protruding into the cavity, by engagement of the catch in a slit or a groove at the distal end of the shank, wherein the first component has a recess into which the second component is fitted.

The tool is provided and designed in particular for a dismantlable medical instrument for micro-invasive procedures in human medicine or veterinary medicine. The tool can be provided and designed to be guided, at the distal end of a medical instrument, through a work channel in an endoscope or another medical instrument.

The first component can be monolithic, i.e. produced in one piece by casting, sintering, forging, or produced from one piece by milling, water-jet cutting, laser cutting, erosion, or produced in one piece by some other means known to one skilled in the art. The cavity for receiving a distal end of a shank can be arranged at the proximal end or near the proximal end of the tool. The cavity can be accessible from the proximal end of the tool, such that the distal end of a shank can be inserted into the cavity from the proximal direction. The cavity can have the shape of a circularly cylindrical or substantially circularly cylindrical blind bore and has a jacket surface in the form of the jacket surface of a circular cylinder.

The second component can have several catches, which are in particular distributed uniformly about the inner circumference of the cavity and at equal angle distances from each other. The catch or catches protrude radially into the cavity from the surface of the cavity, which surface has in particular the shape of the jacket of a circular cylinder. The catch or catches are provided and designed to engage from outside in a slit or an outwardly open groove at the distal end of a shank.

A bayonet connection can be produced in particular by a translational movement of the tool, in a predetermined direction or parallel to a predetermined axis, relative to the distal end of a shank and by a subsequent rotation of the tool, about the predetermined axis, relative to the distal end of the shank. In this case, the slit or the groove at the distal end of the shank has in particular an L-shaped configuration. During the translational movement, the catch is moved through a first limb of the slit or of the groove extending parallel or substantially parallel to the longitudinal axis of the shank, as far as a point where the first limb merges into a second limb substantially orthogonal to the first limb. The second limb of the slit or of the groove extends in particular in the direction of the circumference of the shank. During the rotation of the tool relative to the distal end of the shank, the catch is moved into the second limb of the slit or of the groove. In the state reached in this way, the form-fit engagement between the catch and the second limb of the slit or of the groove connects the tool to the shank in such a way that these cannot be separated from each other by a simple translational movement.

The second component can comprise the catch or the catches or can have solely the catch. A part of the second component, in particular a radially outer end or a radially outer area of the catch, can fill the recess, in particular fills the recess completely. The second component can be joined to the recess or to the edge of the recess in particular with form-fit engagement and cohesive bonding.

The design of the tool such that a cavity for receiving a distal end of a shank is provided on a first component and a catch for forming a bayonet connection is provided on a second component, and such that these two components are then rigidly connected to each other, can permit substantial miniaturization of the tool. Particularly when the tool and the shank have diameters in the range of 2 mm or less, formation of a catch directly on the first component is possible by milling, erosion or in some other way but with very great effort. The design of the catch on a second component provides leeway for further miniaturization of the tool diameter to 1.6 mm or less.

In a tool as described here, the first component comprises in particular a bearing for the movable mounting of a branch or of another movable component of the tool.

The first component can be a fork component, which comprises two parallel or substantially parallel side rails. Between the distal ends of the side rails, a shaft is in particular provided which can be produced in one piece with the fork component. Alternatively, the ends of the shaft can be secured or mounted in bores or other recesses in the distal ends of the side rails of the fork component. The movable branch or the other movable component of the tool is in particular pivotable about a pivot axis defined by the shaft. The tool comprises in particular two movable branches, which are pivotable in opposite directions about the pivot axis defined by the shaft.

By means of a bearing being formed on the first component, it is possible for the tool to be formed exclusively (with the exception of one or more movable branches and mechanisms for their movement) of the first component and of the second component. This simple structure favors miniaturization and reduces the manufacturing costs.

In a tool as described here, the recess on the first component can be a slit which is open at the proximal end, into which the catch is inserted from the proximal direction, and in which the catch is secured.

The catch comprises in particular a radially outer area, which fills the slit, and a radially inner area, which protrudes into the cavity surrounded by the first component.

In a tool as described here, the catch can be cohesively bonded to the edge of the recess.

The catch can be connected to the edge of the recess in particular by means of laser welding or by means of another welding method.

In a tool as described here, the second component comprises in particular the catch and an annular area, said annular area being arranged proximally in relation to the catch.

In a tool as described here, the annular area of the second component can be joined to a proximal edge of the first component.

The design of the second component with an annular area on which one or more catches are provided can simplify the manufacture and the handling of the second component. In particular, the annular area can be easily aligned with the proximal edge of the first component and optionally then joined to the latter.

A tool as described here moreover comprises in particular a transmission mechanism for transmitting a force to a branch or to another movable component of the tool, and a locking projection on the transmission mechanism for engaging in a slit or a groove at a distal end of a shank inserted into the cavity in the first component, in order to lock a bayonet connection between the tool and the shank.

The transmission mechanism comprises in particular a rod or a tube for arrangement in the interior of a shank, the proximal end of which being able to be coupled to an actuation mechanism for the manual movement and for application of a force. The locking projection is in particular a web near the distal end of the transmission mechanism, said web being arranged in the longitudinal direction or parallel to the intended direction of movement of the transmission mechanism. The locking projection can be in particular provided for engagement in a portion of the same slit extending in the longitudinal direction or parallel to the intended direction of movement of the transmission mechanism, in which slit the catch also engages.

In an embodiment, the locking projection and the catch can be in particular designed to engage from radially opposite sides into a slit of a distal end of a shank inserted into the cavity in the first component. The catch and the locking projection are for this purpose designed to engage in the slit from the distal direction.

In particular, the locking projection can be provided and designed to engage from the inside into the slit of a distal end of a shank inserted into the cavity in the first component, wherein the catch engages in the slit from the outside.

In an embodiment, the transmission mechanism comprises in particular a rod or a tube with a slit at the distal end of the rod or tube, and an endpiece with a bearing at the distal end of the endpiece for an articulated mechanical coupling to a movable component of the tool, wherein a proximal end of the endpiece is inserted into the slit at the distal end of the rod or tube and is joined thereto, and wherein an area of the proximal end of the endpiece, protruding laterally from the slit at the distal end of the rod or tube, forms the locking projection.

The bearing at the distal end of the endpiece can be provided for the articulated connection to one or more connecting rods, of which the second ends are each connected in an articulated manner to a branch or to another movable component of the tool in an articulated manner. A translational movement of the transmission mechanism may be linked to a pivoting movement of a branch or of another movable component of the tool by a connecting rod. Alternatively, the branch or the other movable component of the tool could also be connected to the bearing at the distal end of the endpiece without the connecting rods.

The proximal end of the endpiece has in particular a thin and plate-shaped configuration. The lateral edges of the thin plate-shaped proximal end of the endpiece have in particular rectangular or semicircular cross sections. The width of the thin plate-shaped proximal end of the endpiece is in particular larger than the diameter of the rod or tube of the transmission mechanism, such that one or both lateral edges of the thin plate-shaped proximal end of the endpiece protrude from the slit in the distal end of the rod or tube, in order to form one or two locking projections.

Alternatively, the rod or the tube of the transmission mechanism can have a groove at the distal end, such that the jacket surface of the rod or tube is not interrupted in a strip-shaped manner on two opposite sides, but instead only at one location. In this case, the thin plate-shaped proximal end of the endpiece protrudes from the rod or tube of the transmission mechanism only on one side in order to form one locking projection.

The described structure of the transmission mechanism composed of only two components, namely the rod or tube and the endpiece, which nonetheless at the same time form the locking projection, permits a relatively simple structure and cost-effective manufacture.

A shank for a medical tool comprises a shank tube, an L-shaped slit or an L-shaped groove at the distal end of the shank tube, and a support tube at the distal end of the shank, for mechanically supporting and reinforcing the distal end of the shank tube, wherein the section tube is arranged inside the shank tube.

On conventional shanks for medical tools, support tubes can be generally arranged on the outside of the shank tube, wherein the catch of a tool engages from the inside in a groove or a slit in the shank tube. The arrangement of the support tube inside the shank tube allows a catch to engage from the outside in the L-shaped slit or the L-shaped groove at the distal end of the shank tube.

A dismantlable medical instrument comprises a shank and a tool, as described here.

In a medical instrument as described here, the shank comprises in particular a shank tube, an L-shaped slit or an L-shaped groove at the distal end of the shank tube, and a support tube at the distal end of the shank, for mechanically supporting and reinforcing the distal end of the shank tube, wherein the support tube is arranged inside the shank tube.

In a shank as described here, or in a medical instrument as described here, the support tube can have a slit or a groove for receiving the locking projection on the transmission mechanism.

The slit or the groove in the support tube can be straight or L-shaped. In particular, the slit or the groove in the support tube is completely or partly parallel to the longitudinal axis of the shank and to the intended direction of movement of the transmission mechanism of the tool.

The slit or the groove in the support tube can be arranged to be partially or completely congruent with the L-shaped slit or the L-shaped groove at the distal end of the shank tube. In particular, the slit or the groove in the support tube is straight and parallel and is partially or completely congruent with the abovementioned first portion or first limb of the L-shaped slit or of the L-shaped groove at the distal end of the shank tube. A congruent arrangement of mutually corresponding slits in the support tube and in the shank tube can permit particularly deep engagement of the locking projection and/or of the catch and, therefore, particularly good form-fit engagement.

Alternatively, the straight slit or the in particular straight groove in the support tube can be arranged offset with respect to the L-shaped slit or the L-shaped groove, in order to achieve a particularly high degree of stiffness of the distal end of the shank. In the case of a single catch and a single corresponding L-shaped slit or a single corresponding L-shaped groove at the distal end of the shank tube and a single locking projection and a single corresponding slit or a single corresponding groove in the support tube, the slit or the groove in the shank tube, on the one hand, and the slit or the groove in the support tube, on the other hand, are offset from each other by 180 degrees for example. In the case of two slits or grooves at the distal end of the shank tube and/or two slits or grooves in the support tube, the slits or grooves in the shank tube and the slits or grooves in the support tube are arranged in alternation, for example at angle spacings of ca. 90 degrees.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
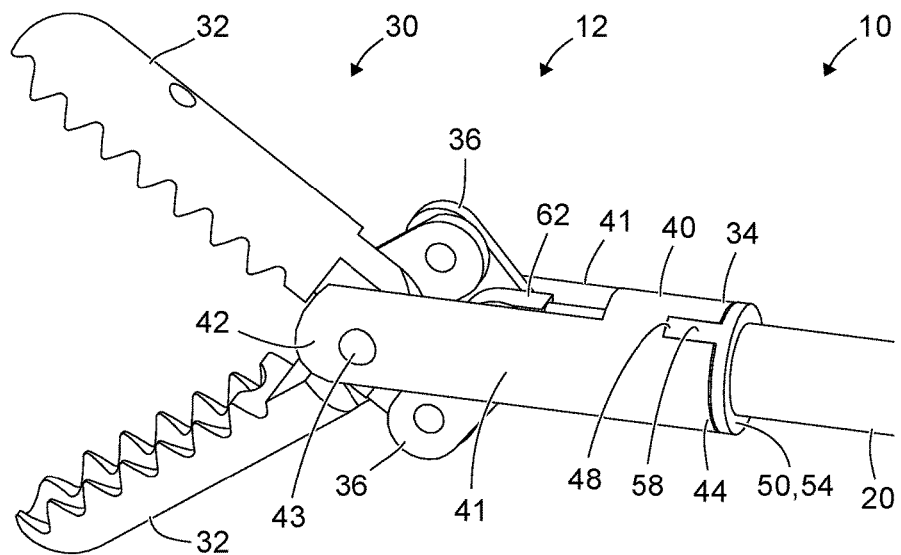
FIG. 1 shows a schematic axonometric view of a distal end of a medical instrument.

FIG. 1 shows a schematic axonometric view of a distal end 12 of a medical instrument 10 for micro-invasive applications in human or veterinary medicine. The medical instrument 10 has a long, thin, rigid or flexible (i.e. elastically deformable, or plastically deformable without destruction), straight or curved shank 20. The distal of the shank 20 is mechanically connected to a tool 30, in particular to the proximal end 34 thereof, in such a way as to be releasable without destruction. A manipulation mechanism for manually manipulating the medical instrument 10 can be provided at the proximal end of the shank 20.

The tool 30 comprises two branches 32 which are pivotable in opposite directions about the same pivot axis and which serve for the gripping, pinching, electrosurgical coagulation or cutting of tissue. The tool 30 comprises a first component or fork component 40 and a second component or catch component 50. The fork component 40 comprises two parallel side rails 41, of which the distal ends 42 form the distal end of the fork component 40. A bearing 43 for the pivotable branches 32 is provided at the distal ends 42 of the side rails 41. The bearing 43 is formed by a shaft connecting the distal ends 42 of the side rails 41. The shaft defines the common pivot axis of the pivotable branches 32.

The proximal end of the fork component 40 is formed by a substantially circular proximal edge 44 of the fork component 40. The proximal edge 44 of the fork component 40 is interrupted by two slits 48 arranged opposite each other, of which only one is visible in FIG. 1. The slits 48 each have a substantially rectangular shape.

The catch component 50 comprises an annular area 54, which is arranged parallel to the proximal edge 44 of the fork component 40 and can be joined thereto, in particular connected thereto by welding. The catch component 50 moreover comprises two catches which lie opposite each other and of which the radially outer ends or areas 58 fill the slits 48 at the proximal end of the fork component 40 and are joined thereto. In particular, the edges of the radially outer areas 58 of the catches of the catch component 50 are connected to the edges of the slits 48 by welding or soldering.

A transmission mechanism is arranged in the shank 20 and in the fork component 40 of the tool 30, which transmission mechanism, in the view in FIG. 1, is largely concealed by the shank 20 and the fork component 40 of the tool 30. Only an endpiece 62 forming the distal end of the transmission mechanism is partially visible in FIG. 1 between the side rails 41 of the fork component 40 of the tool 30. The transmission mechanism is displaceable within a predetermined range inside the shank 20 and the fork component 40 of the tool 30 in a direction parallel to the longitudinal axis of the shank 20. The proximal end of the transmission mechanism is coupled, for example, to a pivotable part of said manipulation mechanism at the proximal end of the shank 20. The endpiece 62 forming the distal end of the transmission mechanism is coupled in an articulated manner to the branches 32, in each case via a connecting rod 36, in such a way that a translational movement of the transmission mechanism is associated with a pivoting movement of the branches 32 of the tool 30.

Figure 2:
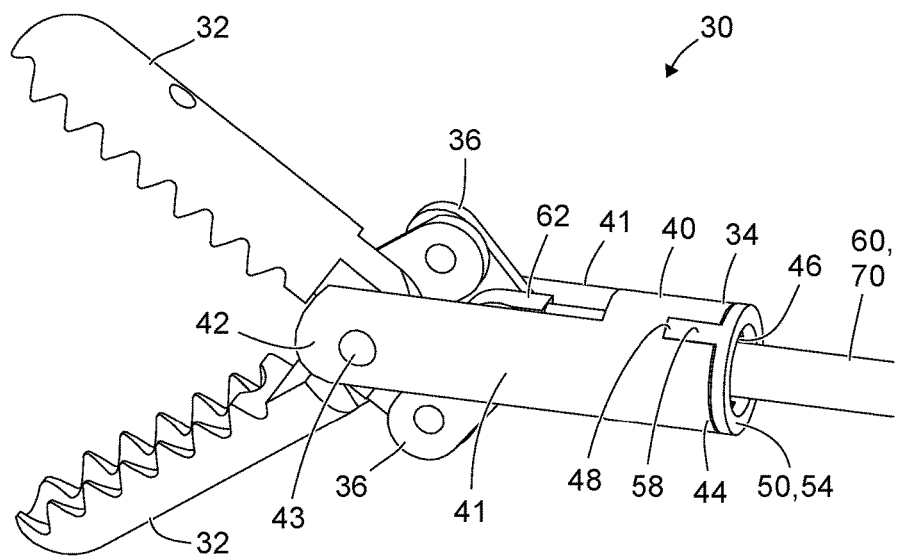
FIG. 2 shows a schematic axonometric view of a tool of the medical instrument from FIG. 1.

FIG. 2 shows a schematic axonometric view of the tool 30 from FIG. 1. The nature of the view, in particular the viewing direction, substantially corresponds to that of FIG. 1.

Only the tool 30 is shown in FIG. 2, not the shank 20 of the medical instrument. Therefore, a further part of the transmission mechanism 60 is visible in FIG. 2, namely a rod 70 that is provided for arrangement in the shank 20 of the medical instrument 10 (cf. FIG. 1).

Moreover, the annular structure of the annular area 54 and a cavity 46 in the fork component 40 can be seen in FIG. 2.

Figure 3:
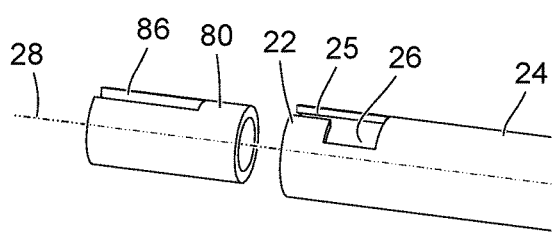
FIG. 3 shows a schematic axonometric view of constituent parts of a shank of the medical instrument from FIG. 1.

FIG. 3 shows a schematic axonometric view of constituent parts of the shank 20 of the medical instrument 10 from FIG. 1. The nature of the view, in particular the viewing direction, substantially corresponds to that of FIGS. 1 and 2.

The shank comprises a shank tube 24, of which the position in FIG. 3 in the horizontal direction corresponds to the position in FIG. 1. Two L-shaped slits arranged opposite each other are provided at the distal end 22 of the shank tube 24, of which only one slit is visible in FIG. 3. Each L-shaped slit comprises a first portion 25, which extends parallel to the longitudinal axis 28 of the shank tube 24, and a second portion 26, which extends in a direction parallel to the circumference of the shank tube 24.

FIG. 3 moreover shows a support tube 80 which, when the shank has been made ready for use in the intended manner, is arranged at the distal end 22 of the shank inside the shank tube 24. In FIG. 3, the support tube 80 is shown outside the shank tube 24, i.e. having been withdrawn in the distal direction from the shank tube 24 in a direction parallel to the longitudinal axis 28 of the shank. With the shank made ready for use in the intended manner, the support tube 80 is arranged in the shank tube 24 particularly in such a way that the distal edge of the support tube 80 and the distal edge of the shank tube 24 lie in one plane.

The support tube 80 has two straight slits 86 which are each rectangular or substantially rectangular and which lie opposite each other, of which only one slit is visible in FIG. 3. The slits 86 are parallel to the longitudinal axis 28 of the shank and therefore also parallel to the intended direction of movement of the transmission mechanism 60 (cf. FIG. 2).

In the intended arrangement of the support tube 80 in the shank tube 24, the slits 86 in the support tube 80, on the one hand, and the first portions 25 of the L-shaped slits in the shank tube 24, on the other hand, are congruent or substantially congruent. When the shank 20 has been made ready, the support tube 80 is connected to the shank tube 24 in particular by cohesive bonding (for example by laser welding or soldering) and optionally in addition with frictional engagement or force-fit engagement. The support tube 80 reinforces the distal end 22 of the shank. Moreover, the inner cross section of the support tube 80 (apart from the slits 86) corresponds substantially to the outer cross section of the rod 70 of the transmission mechanism 60 (cf. FIG. 2), such that the transmission mechanism 60 is guided in the support tube 80 with minimal play and friction.

Moreover, the outer cross section of the shank tube 24 and therefore of the shank corresponds at the distal end 22 thereof (apart from the L-shaped slits 25, 26) to the cross section of the cavity 46 (apart from the catches) at the proximal end of the fork component 40 (cf. FIGS. 2, 5 and 6), such that the distal end 22 of the shank 20 is guided with minimal play in the cavity 46 in the fork component 40.

Figure 4:
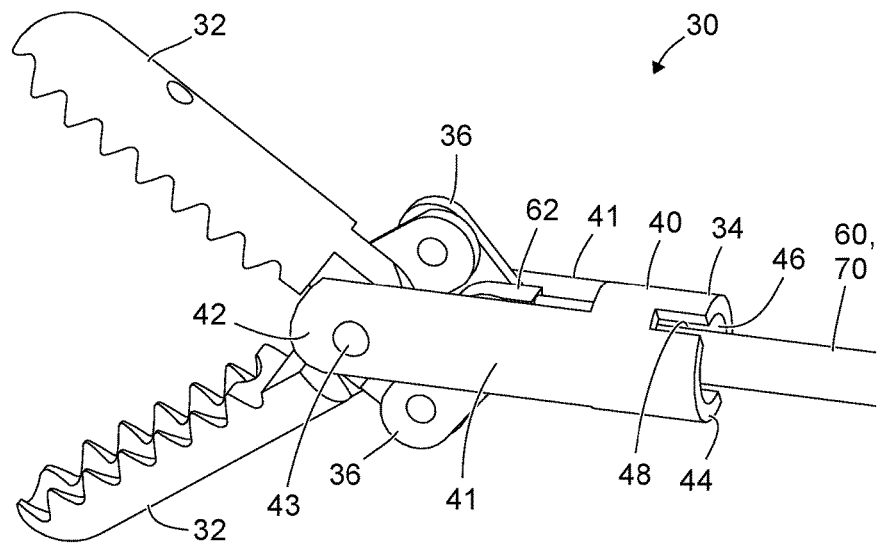
FIG. 4 shows a further schematic axonometric view of parts of the tool from FIGS. 1 and 2.

FIG. 4 shows a further schematic axonometric view of parts of the tool 30 from FIG. 2. The nature of the view, in particular the viewing direction, substantially corresponds to that of FIGS. 1 and 2.

In FIG. 4, the tool 30 is shown without the catch component 50. The slits 48 in the fork component 40 are therefore visible, which slits 48 start from the substantially circular proximal edge 44 of the fork component 40 and interrupt said edge.

Figure 5:
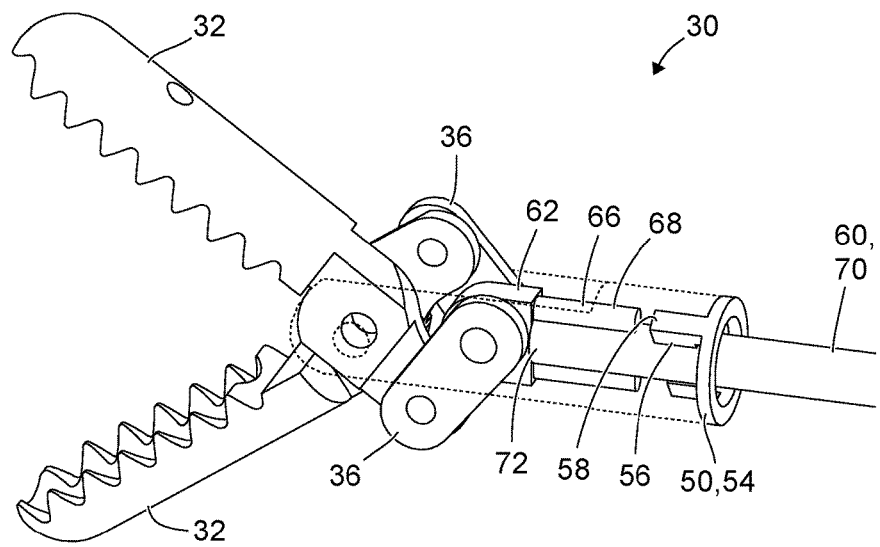
FIG. 5 shows a further schematic axonometric view of parts of the tool from FIGS. 1 and 2.

FIG. 5 shows a further schematic axonometric view of the tool 30 from FIGS. 2 and 4. The nature of the view, in particular the viewing direction, substantially corresponds to that of FIGS. 1, 2 and 4.

In FIG. 5, the fork component 40 of the tool 30 is depicted in transparent form and is indicated only by the contours thereof that are visible in the chosen viewing direction. Therefore, the catches 56 arranged in the distal direction from the annular area 54 of the catch component 50 are visible in FIG. 5, their outer ends or areas 58 filling the slits 48 in the fork component 40 (cf. FIG. 4). The radially inner ends of the catches 56 extend into the cavity 46 at the proximal end of the fork component 40 (cf. FIG. 4).

Moreover, the transmission mechanism 60 is largely visible in FIG. 5. The transmission mechanism 60 comprises a rod 70 and an endpiece 62, which forms the distal end of the transmission mechanism 60. The endpiece 62 comprises a distal end 64 with a bearing for the articulated connection to the connecting rods 36, and a substantially thin and plate-shaped proximal end 66, which is arranged in a slit at the distal end 72 of the rod 70. Edges of the thin plate-shaped proximal end 66 of the endpiece 62 that protrude laterally from the slit at the distal end 72 of the rod 70 form two web-shaped locking projections 68. The locking projections 68 each extend parallel to the longitudinal axis of the rod 70 of the transmission mechanism 60 and thus also parallel to the longitudinal axis 28 of the shank 20 (cf. FIG. 3) and to the slits 86 in the support tube 80.

Figure 6:
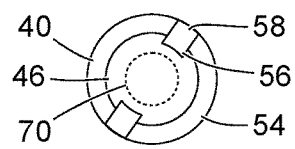
FIG. 6 shows a schematic view of part of the tool from FIGS. 1, 2, 4 and 5.

FIG. 6 shows a schematic view of the catch component 50 as seen from the distal direction. For orientation purposes, the contour of the cross section of the rod 70 of the transmission mechanism 60 (cf. FIG. 5) is also indicated by a broken line.

The inner contour of the annular area 54 of the catch component 50 corresponds to the contour of the cross section of the cavity 46 at the proximal end of the fork component 40 (cf. FIGS. 2 and 4). The catches 56 engage from outside in the cavity 46.

The widths of the catches 56 correspond to the widths of the first portions 25 of the L-shaped slits in the shank tube 24, such that the catches can be guided with minimal friction through the first portions 25 of the L-shaped slits in the shank tube 24. If the catches 56 engage so deeply in the cavity 46 that they also engage in the slits 86 in the support tube 80 (cf. FIG. 3), the slits 86 in the support tube 80 are also at least as wide as the catches 56 and, in contrast to the view in FIG. 3, are L-shaped.

The lengths of the catches (each measured in a direction parallel to the longitudinal axis 28 of the shank; cf. FIG. 3) correspond to the dimensions of the second portions 26 of the L-shaped slits in the shank tube 24, such that the catches 56 can be inserted with minimal friction into the second portions 26 of the L-shaped slits.

Figure 7:
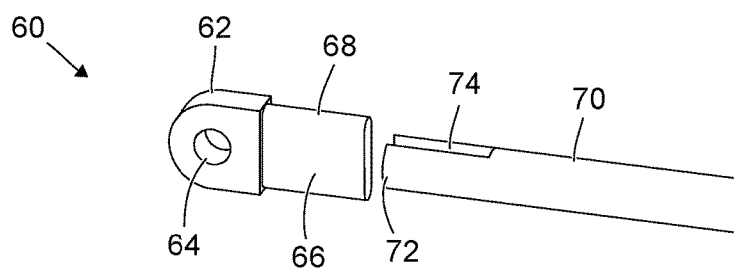
FIG. 7 shows a further schematic axonometric view of parts of the tool from FIGS. 1 and 2.

FIG. 7 shows a further schematic axonometric view of constituent parts of the transmission mechanism 60 of the tool 30 from FIGS. 1 and 2. In FIG. 7, the endpiece 62 is shown in a position offset distally in relation to the rod 70. Therefore, FIG. 7 clearly shows, on the one hand, the slit 74 at the distal end 72 of the rod 70, and, on the other hand, the thin plate-shaped proximal end 66 of the endpiece 62. The lateral edges of the proximal end 66 of the endpiece 62, which extend parallel to the longitudinal axis of the rod 70, form the locking projections 68. In the example shown, the locking projections 68 have rounded cross sections.

Figure 8:
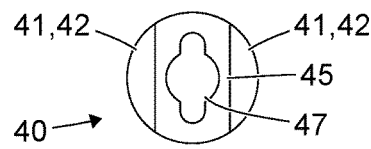
FIG. 8 shows a further schematic view of part of the tool from FIGS. 1 and 2.

FIG. 8 shows a schematic view of the fork component 40 of the tool 30 from FIGS. 1 and 2, as seen from the distal direction.

Between the proximal ends of the side rails 41, on the one hand, and the distal end of the cavity 46 (cf. FIG. 4), on the other hand, the fork component 40 has a wall 45, which is not visible in the other figures. This wall 45 is in particular substantially plate-shaped and flat and delimits the cavity 46 in the distal direction or forms the distal surface of the cavity 46.

A continuous bore 47 is provided in the wall 45. The continuous bore 47 extends, in the axial direction of the fork component 40 and thus in a direction orthogonal with respect to the drawing plane of FIG. 9, from the space between the side rails 41, on the one hand, to the cavity 46 at the proximal end of the fork component 40 (cf. FIGS. 2 and 4; not visible in FIG. 9), on the other hand.

The continuous bore 47 has a cross section corresponding substantially to the cross section of the transmission mechanism 60 in the transition area between the endpiece 62 and the rod 70 (cf. FIGS. 5 and 7), such that the transmission mechanism 60 is guided in the continuous bore 47 in the fork component 40 with minimal play and friction. The cross section of the transmission mechanism 60 in the transition area between the endpiece 62 and the rod 70 (cf. FIGS. 5 and 7) and the cross section of the continuous bore 47 are each non-circular. In particular, the cross section of the transmission mechanism 60 deviates from a purely circular shape as a result of the locking projections 68 (cf. FIG. 5). In this way, a rotation of the transmission mechanism 60 relative to the fork component 40 is suppressed by form-fit engagement.

Figure 9:
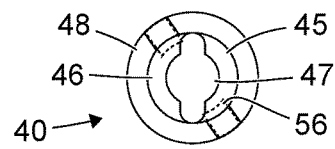
FIG. 9 shows a further schematic view of the part from FIG. 1.

FIG. 9 shows a further schematic view of the fork component 40 of the tool 30 from FIGS. 1 and 2. In FIG. 9, the fork component 40 is shown in a view from the proximal direction. Thus, the fork component 40 is shown from opposite directions in FIGS. 8 and 9.

FIG. 9 shows the continuous bore 47, the substantially circularly cylindrical cavity 46 at the proximal end of the fork component 40, and the two slits 48 lying opposite each other in the fork component 40. The contours of the catches 56 protruding into the cavity 46, and belonging to the catch component 50 (cf. FIGS. 1, 2, 5 and 6), not shown in FIG. 9, are indicated by broken lines.

As has already been mentioned, the transmission mechanism 60 is guided in the fork component 40 (cf. FIGS. 8 and 9) by form-fit engagement between the transition area between the rod 70 and the endpiece 62, in particular the locking projections 68, on the one hand, (cf. FIGS. 5 and 7), and the continuous bore 47 in the fork component 40, on the other hand, in such a way that the transmission mechanism 60 can be displaced in the longitudinal direction relative to the fork component 40 but cannot be rotated. Alternatively, a similar guide can be achieved by form-fit engagement between the connecting rods 36, the distal end 64 of the endpiece 62 of the transmission mechanism 60 and the mutually facing surfaces of the side rails 41 of the fork component 40 (cf. FIGS. 2 and 4).

The function of the components of the tool 30 and of the shank 20 will be clear from the overview of the figures.

For the releasable mechanical connection of the tool 30 to the shank 20, the transmission mechanism 60, in particular the rod 70 of the transmission mechanism 60 (cf. FIG. 2), is first of all inserted into the shank 20 (cf. FIG. 3) from the distal direction.

The branches 32 of the tool 30 are brought to a beyond open position, in which the angle between the branches 32 is greater than that shown in FIGS. 1, 2, 4 and 5. In this beyond open position, the locking projections 68 on the transmission mechanism 60 assume their farthest distal position, in which they engage in the continuous bore 47 in the fork component 40 but do not protrude into the cavity 46 at the proximal end of the fork component 40.

The shank 20 and the tool 30 are brought together until the distal end 22 of the shank 20 is inserted completely into the cavity 46 in the fork component 40 of the tool 30 and the distal end 22 of the shank 20 bears on the wall 45 of the fork component 40. The catches 56 are thereby inserted into the first portions 25 of the L-shaped slits at the distal end 22 of the shank 20. When the distal end 22 of the shank 20 bears on the wall 45 in the fork component 40, the catches 56 are located in the transition areas between the first portions 25 and the second portions 26 of the L-shaped slits at the distal end 22 of the shank tube 24 (cf. FIG. 3).

The shank 20 can now be rotated clockwise (viewed from the proximal direction) about its axis 28 relative to the tool 30. In doing so, the catches 56 are moved away from the first portions 25 into the second portions 26 of the L-shaped slits at the distal end 22 of the shank 20.

When the catches 56 bear on the ends, remote from the first portions 25, of the second portions 26 of the L-shaped slits at the distal end 22 of the shank 20, shank 20 and tool 30 are located in their intended relative positions, in which shank 20 and tool 30 cannot be separated from each other by a simple translational movement. In this intended position of the shank 20 relative to the tool 30, the locking projections 68 on the transmission mechanism 60 (cf. FIG. 5) are aligned with the slits 86 in the support tube 80 and with the first portions 25 of the L-shaped slits at the distal end 22 of the shank tube 24 (cf. FIG. 3). The transmission mechanism 60 can therefore be moved in the proximal direction relative to the tool 30 and to the shank 20, whereupon the branches 32 leave their beyond open position. In doing so, the locking projections 68 on the transmission mechanism 60 engage in the slits 86 in the support tube 80 and the first portions 25 of the L-shaped slits in the shank tube 24. By means of this engagement, the tool 30 can no longer be rotated relative to the shank 20, and the catches 56 cannot be moved to the first portions 25 of the L-shaped slits in the shank tube 24. In this way, the mechanical connection between shank 20 and tool 30 is locked as long as the branches 32 are not located in their beyond open position.

A movement to the beyond open position 32 can be suppressed by mechanisms at the distal ends of the shank 20 and of the transmission mechanism 60, in particular in a manipulation mechanism.

In the ideal case free of play, the distal edge or the distal end 22 of the shank tube 24 (cf. FIG. 3) bears on the wall 45 in the fork component 40 (cf. FIGS. 8 and 9), on the one hand, while at the same time, on the other hand, the distal ends or edges of the catches 56 (cf. FIG. 5) bear on the distal edges of the second portions 26 of the L-shaped slits in the shank tube 24 (cf. FIG. 3). A longitudinal play of the mechanical connection between shank 20 and tool 30 is defined by the difference between the distance of the distal edges or flanks of the catches 56 (cf. FIG. 5) and the wall 45 in the fork component 40 (cf. FIGS. 8 and 9), on the one hand, and the distance between the distal edges of the second portions 26 of the L-shaped slits in the shank tube 24 and the distal end 22 of the shank tube 24, on the other hand.

In FIGS. 1 and 2, a small distance is indicated between the annular area 54 of the catch component 50, on the one hand, and the proximal edge 44 of the fork component 40, on the other hand. This small distance can be bridged or filled by a welded or soldered seam. In other words, the dimensions of the two catches 56 measured in a direction parallel to the longitudinal axis 28 of the shank 20 are slightly greater than the depths, measured in the same direction, of the slits 48 in the fork component. This ensures that, when the catches 56 are pushed into the slits 48, the positions of the catches 56 are defined unambiguously, with a form fit, by the abutment of the catches 56 or of their outer areas 58 against the distal ends of the slits 48 in the fork component 40. In these positions defined unambiguously by a form-fit engagement, the outer areas 58 of the catches 56 are joined to the slits 48 or to the edges of the slits 48, in particular connected thereto by laser welding.

The distances defining the mechanical play between shank 20 and tool 30 are therefore each defined on a single component. On the shank 20, this is the distance between the distal edge or end 22 of the shank tube 24 and the distal edge of the second portion 26 of the L-shaped slit in the shank tube 24. On the tool, this is the distance between the proximal surface of the wall 45 in the fork component 40 and the distal ends of the slits 48 in the fork component, on which the distal end faces of the outer areas 58 of the catches 56 bear. Since both distances determining the play are each defined on a single component, the play can be set particularly precisely and, consequently, can also be particularly small.

For the non-destructive release of the mechanical connection between shank 20 and tool 30, a blocking of the beyond open position can optionally be canceled first of all via the manipulation mechanism. Thereafter, the branches 32 are moved to their beyond open position and the transmission mechanism 60 is moved with the locking projections 68 to its farthest distal position. In this configuration, the locking projections 68 on the transmission mechanism 60 (cf. FIG. 5) no longer engage in the slits 86 in the support tube 80 and in the first portions 25 of the L-shaped slits in the shank tube 24 (cf. Figure). The tool 30 can be rotated counterclockwise (viewed from the distal direction) relative to the shank 20. In doing so, the catches 56 engaging from the outside in the second portions 26 are moved as far as the transition areas between the second portions 26 and the first portions 25 of the L-shaped slits in the shank tube 24. Thereafter, shank 20 and tool 30 can be pulled apart from each other. In doing so, the catches 56 are moved into the first portions 25 of the L-shaped slits in the shank tube 24 and are pulled out of the latter.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A tool for a dismantlable medical instrument having a shank, the tool comprising:
    a first component that surrounds a cavity for receiving a distal end of the shank;
    a second component with a catch that protrudes into the cavity surrounded by the first component to form a bayonet connection, the distal end of the shank configured to protrude into the cavity by engagement of the catch in a slit or a groove at the distal end of the shank;
    further wherein the second component includes a ring-shaped portion and wherein the catch protrudes from the ring-shaped portion in an axial direction of the second component; and
    a recess formed in the first component into which the second component is fitted, the recess being open at an exterior surface of the first component and being open at an opposing interior surface of the first component, such that, in a radial direction of the first component, the recess forms a through-hole.

2. The tool according to claim 1, wherein the first component comprises a bearing for the movable mounting of a branch or another movable component of the tool.

3. The tool according to claim 1, wherein, in an axial direction of the first component, the recess on the first component is a slit that is open at a proximal end of the first component, wherein the catch is inserted into the recess from the proximal direction and is secured in the recess.

4. The tool according to claim 1, wherein the catch is cohesively bonded to an edge of the recess.

5. The tool according to claim 1, wherein the second component comprises an annular area arranged proximally in relation to the catch.

6. The tool according to claim 5, wherein the annular area of the second component is joined to a proximal edge of the first component.

7. The tool according to claim 1, further comprising:
    a transmission mechanism for transmitting a force to a branch or to another movable component of the tool; and
    a locking projection on the transmission mechanism for engaging in the slit or the groove at the distal end of the shank inserted into the cavity in the first component to lock a bayonet connection between the tool and the shank.

8. The tool according to claim 7, wherein the transmission mechanism comprises:
    a rod or a tube with a slit at a distal end of the rod or tube; and
    an endpiece with a bearing at the distal end of the endpiece for an articulated mechanical coupling to a movable component of the tool,
    wherein a proximal end of the endpiece is inserted into the slit at the distal end of the rod or tube and is joined thereto, and
    wherein an area of the proximal end of the endpiece, protruding laterally from the slit at the distal end of the rod or tube, forms the locking projection.

9. The tool according to claim 8, wherein the first component includes an interior wall, the interior wall having a bore extending therethrough, the bore having a contour that corresponds to the rod or the tube and the locking projection of the transmission mechanism, such that the rod or the tube and the locking mechanism can be axially inserted through the bore.

10. A dismantlable medical instrument comprising: the shank; and the tool according to claim 1.

11. A medical instrument according to claim 10, wherein the shank comprises:
    a shank tube;
    an L-shaped slit or an L-shaped groove at the distal end of the shank tube; and
    a support tube at the distal end of the shank for mechanically supporting and reinforcing the distal end of the shank tube, wherein the support tube is arranged inside the shank tube.

12. The medical instrument according to claim 11, wherein the support tube has a slit or a groove for receiving a locking projection on a transmission mechanism.

13. The tool according to claim 1, wherein the first component is a single, monolithic component.

* * * * *